US012629204B2

(12) United States Patent
Beeckler et al.

(10) Patent No.: US 12,629,204 B2
(45) Date of Patent: May 19, 2026

(54) FOLDING FAN CATHETER WITH ELECTRODES

(71) Applicant: Biosense Webster (Israel) Ltd., Yokneam (IL)

(72) Inventors: Christopher Thomas Beeckler, Brea, CA (US); Assaf Govari, Haifa (IL); Joseph Thomas Keyes, Sierra Madre, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 18/583,279

(22) Filed: Feb. 21, 2024

(65) Prior Publication Data

US 2024/0245453 A1 Jul. 25, 2024

Related U.S. Application Data

(62) Division of application No. 17/065,456, filed on Oct. 7, 2020, now Pat. No. 11,918,281.

(51) Int. Cl.
*A61B 18/14* (2006.01)
*A61B 17/00* (2006.01)
*A61B 18/00* (2006.01)

(52) U.S. Cl.
CPC .................... *A61B 18/1492* (2013.01); *A61B 2017/00526* (2013.01); *A61B 2018/00077* (2013.01);

(Continued)

(58) Field of Classification Search
CPC ............ A61B 18/1206; A61B 18/1492; A61B 2018/00077; A61B 2018/0016; A61B 2018/00214; A61B 2018/00357; A61B 2018/00577; A61B 2018/00613; A61B 2018/00791; A61B 2018/00839; A61B 2018/00875; A61B 2018/124;
(Continued)

(56) References Cited

U.S. PATENT DOCUMENTS

| | | | |
|---|---|---|---|
| 5,391,199 A | 2/1995 | Ben-Haim | |
| 5,505,730 A | 4/1996 | Edwards | |

(Continued)

FOREIGN PATENT DOCUMENTS

| | | |
|---|---|---|
| CN | 204192679 U | 3/2015 |
| CN | 106175853 A | 12/2016 |

(Continued)

OTHER PUBLICATIONS

Extended European Search Report dated Mar. 10, 2022, from corresponding European Application No. 21201097.9.
(Continued)

*Primary Examiner* — Khadijeh A Vahdat

(57) ABSTRACT

An apparatus includes a shaft and a folding fan catheter. The shaft is configured for insertion through a sheath into a cavity of an organ of a patient. The folding fan catheter is fixed to a distal end of the shaft and includes (a) a resilient foldable frame, which is fixed to the distal end of the shaft and is configured to be unfolded so as to assume a fan shape, (b) one or more flexible surfaces, coupled to the frame to form a fan-shaped surface when the frame is unfolded, and (c) a plurality of electrodes that are disposed over the one or more flexible surfaces and are configured to contact tissue.

20 Claims, 6 Drawing Sheets

(52) U.S. Cl.
CPC ............... *A61B 2018/00214* (2013.01); *A61B 2018/00577* (2013.01); *A61B 2018/00613* (2013.01); *A61B 2562/166* (2013.01)

(58) Field of Classification Search
CPC .... A61B 2018/1467; A61B 2018/1475; A61B 2018/162; A61B 2017/00084; A61B 2017/00243; A61B 2017/00526; A61B 2017/00867; A61B 2034/2051; A61B 2034/2053; A61B 2034/2072

See application file for complete search history.

(56) References Cited

U.S. PATENT DOCUMENTS

| | | |
|---|---|---|
| 5,846,196 A | 12/1998 | Siekmeyer et al. |
| 5,904,711 A | 5/1999 | Flom et al. |
| 6,024,743 A | 2/2000 | Edwards |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 7,367,975 B2 | 5/2008 | Malecki et al. |
| 7,756,576 B2 | 7/2010 | Levin |
| 7,848,787 B2 | 12/2010 | Osadchy |
| 7,869,865 B2 | 1/2011 | Govari et al. |
| 8,133,221 B2 | 3/2012 | Malecki |
| 9,480,525 B2 | 11/2016 | Lopes et al. |
| 9,492,228 B2 | 11/2016 | Lopes et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2005/0085880 A1 | 4/2005 | Truckai et al. |
| 2007/0123851 A1 | 5/2007 | Alejandro et al. |
| 2007/0123852 A1 | 5/2007 | Deem et al. |
| 2010/0204560 A1 | 8/2010 | Salahieh et al. |
| 2010/0305562 A1 | 12/2010 | Winkler et al. |
| 2010/0331883 A1 | 12/2010 | Schmitz et al. |
| 2013/0053851 A1 | 2/2013 | Schmitz et al. |
| 2013/0096550 A1 | 4/2013 | Hill |
| 2014/0039491 A1 | 2/2014 | Bakos et al. |
| 2015/0374252 A1 | 12/2015 | de la Rama et al. |
| 2018/0042667 A1 | 2/2018 | Pappone et al. |
| 2019/0183372 A1 | 6/2019 | Ruppersberg |
| 2019/0282116 A1 | 9/2019 | Olson |
| 2019/0328274 A1 | 10/2019 | Gliner et al. |
| 2019/0365463 A1 | 12/2019 | Govari |

FOREIGN PATENT DOCUMENTS

| | | |
|---|---|---|
| JP | H10511589 A | 11/1998 |
| JP | 2008503269 A | 2/2008 |
| JP | 2014530644 A | 11/2014 |
| WO | 1996005768 A1 | 2/1996 |
| WO | 2010056771 A1 | 5/2010 |

OTHER PUBLICATIONS

Exam Report dated Feb. 26, 2025, from corresponding European Application No. 21201097.9.

Notice of Reasons for Refusal with English translation dated Apr. 30, 2025, from corresponding Japense Application No. 2021-164634.

First Search dated Jan. 22, 2026, from corresponding Chinese Application No. 202111173900.2.

First Office Action with English translation dated Jan. 22, 2026, from corresponding Chinese Application No. 202111173900.2.

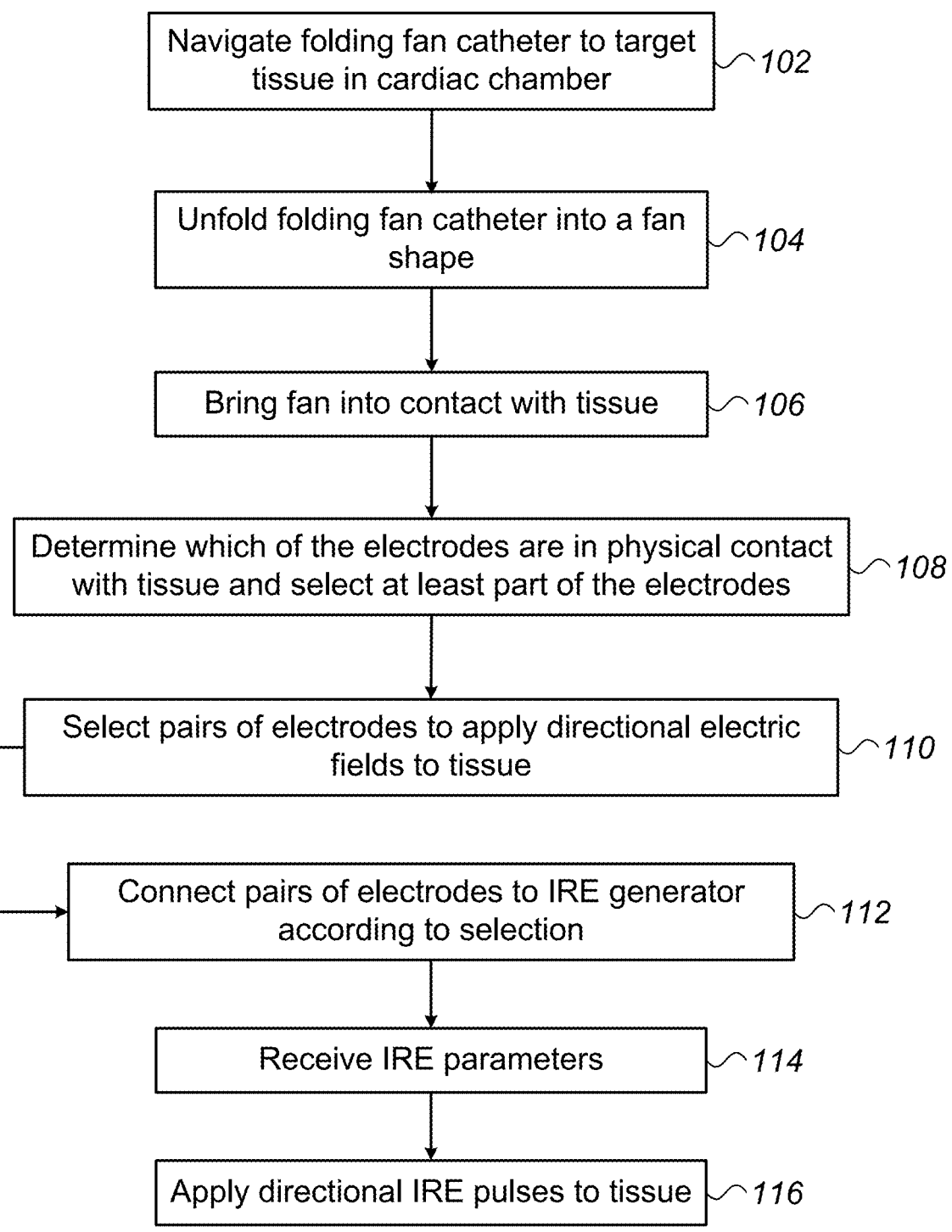

Navigate folding fan catheter to target tissue in cardiac chamber    ⌇102

Unfold folding fan catheter into a fan shape    ⌇104

Bring fan into contact with tissue    ⌇106

Determine which of the electrodes are in physical contact with tissue and select at least part of the electrodes    ⌇108

Select pairs of electrodes to apply directional electric fields to tissue    ⌇110

Connect pairs of electrodes to IRE generator according to selection    ⌇112

Receive IRE parameters    ⌇114

Apply directional IRE pulses to tissue    ⌇116

FOLDING FAN CATHETER WITH ELECTRODES

CROSS-REFERENCE TO RELATED APPLICATIONS

This application is a divisional of prior filed U.S. patent application Ser. No. 17/065,456 filed on Oct. 7, 2020, now U.S. Pat. No. 11,918,281, which prior application is hereby incorporated by reference as if set forth in full into this application.

FIELD OF THE INVENTION

The present invention relates generally to medical probes, and particularly to multi-electrode catheters.

BACKGROUND OF THE INVENTION

Various medical probes with distal-end geometries designs suited for treating specific tissue were proposed in the patent literature. For example, U.S. Pat. No. 8,133,221 describes methods for treating anatomic tissue defects such as patent foramen ovale (PFO). The method generally involves positioning a distal end of an elongate catheter device at the site of the anatomic defect, exposing an expandable housing and energy transmission member out of the distal end of the catheter device, engaging the housing with tissues at the site of the anatomic defect, applying suction to the tissues via the housing to bring the tissues together; and applying energy to the tissues with the energy transmission member to substantially close the anatomic defect acutely. Apparatus generally include an elongate catheter body, a housing extending from a distal end of the catheter body for engaging tissues at the site of the anatomic defect, and an energy transmission member adjacent a distal end of the housing, the energy transmission member having at least one substantially planar surface.

As another example, U.S. Pat. No. 9,492,228 describes systems, methods, and devices that allow intravascular or percutaneous mapping, orientation and/or ablation, in bodily cavities or lumens. A device includes elongate members, moveable between an unexpanded configuration and an expanded or fanned configuration. The elongate members form a stack in the unexpanded configuration to fit through a catheter sheath. The elongate members follow respective arcuate or curvilinear paths as advanced from the sheath into the bent or coiled stack configuration, adopting volute, scroll or rho shapes, and may be nested. The elongated members are fanned or radially spaced circumferentially with respect to one another into the expanded or fanned configuration. Transducer elements carried by elongate members sense various physiological characteristics of or proximate tissue, and/or may apply energy to or proximate tissue. The elongate members are rotatable in groups or as a group in the expanded configuration. The device is retractable.

U.S. Pat. No. 5,904,711 describes methods and apparatus for thoracoscopic defibrillation of a patient's heart. The technique involves introducing a first electrode through a percutaneous intercostal penetration, positioning the first electrode against the heart surface and positioning a second electrode against the patient's body. A voltage is then applied through the percutaneous intercostal penetration to the first electrode and to a second electrode to deliver electrical energy to the first electrode, through at least a portion of the patient's heart, and to the second electrode. The electrical energy applies an electric charge to the patient's heart to defibrillate the heart muscle or restart the heart during, for example, cardiac procedures that involve arresting the heart.

SUMMARY OF THE INVENTION

An embodiment of the present invention that is described hereinafter provides an apparatus including a shaft and a folding fan catheter. The shaft is configured for insertion through a sheath into a cavity of an organ of a patient. The folding fan catheter is fixed to a distal end of the shaft and includes (a) a resilient foldable frame, which is fixed to the distal end of the shaft and is configured to be unfolded so as to assume a fan shape, (b) one or more flexible surfaces, coupled to the frame to form a fan-shaped surface when the frame is unfolded, and (c) a plurality of electrodes that are disposed over the one or more flexible surfaces and are configured to contact tissue.

In some embodiments, the resilient foldable frame is made at least partially of a shape memory alloy having a self-configurable preformed shape including, when unconstrained, one of a folded fan shape and an unfolded fan shape.

In some embodiments, the resilient foldable frame includes a plurality of splines.

In an embodiment, the splines are strip-shaped, and are configured to overlap when the frame is folded. In another embodiment, each strip-shaped spline is configured to bend about a longitudinal axis of the spline when the frame unfolds, such that when the frame is unfolded, the strip-shaped splines lie in a plane of the fan-shaped surface.

In an embodiment, the preformed shape of the frame includes the folded fan shape, and further includes puller wires that are attached to distal ends of the splines and are configured to, when pulled, pull the frame apart into the unfolded fan shape. In another embodiment, the preformed shape of the frame includes the unfolded fan shape, and the frame is configured to be collapsed upon withdrawal back into the sheath.

In some embodiments, the one or more flexible members include one or more flexible printed circuit boards (PCBs), and the electrodes are formed in one or more electrically-conductive layers of the PCBs.

There is additionally provided, in accordance with another embodiment of the present invention, a method including inserting into a cavity of an organ of a patient, through a sheath, a folding fan catheter fixed to a distal end of a shaft, the folding fan catheter including (a) a resilient foldable frame, which is fixed to the distal end of the shaft and is configured to be unfolded so as to assume a fan shape, (b) one or more flexible surfaces, coupled to the frame to form a fan-shaped surface when the frame is unfolded, and (c) a plurality of electrodes that are disposed over the one or more flexible surfaces and are configured to contact tissue. After the folding fan catheter exits the sheath in the cavity and the resilient inner end section assumes the fan shape, contact is made between the plurality of electrodes and tissue, and a medical procedure is performed using the electrodes.

In some embodiments, inserting the catheter includes, if the preformed shape includes the unfolded fan shape, allowing the frame to self-expand.

There is further provided, in accordance with another embodiment of the present invention, a method of manufacturing a folding fan catheter, the method including fixing to a distal end of a shaft a resilient foldable frame, which is configured to be unfolded so as to assume a fan shape. One or more flexible surfaces are coupled to the frame, to form a fan-shaped surface when the frame is unfolded. A plurality of electrodes is disposed over the one or more flexible surfaces, wherein the electrodes are configured to contact tissue.

The present invention will be more fully understood from the following detailed description of the embodiments thereof, taken together with the drawings in which:

BRIEF DESCRIPTION OF THE DRAWINGS

FIG. 4 is a flow chart that schematically illustrates a method of irreversible electroporation (IRE) using the folding fan catheter of FIGS. 2A and 2B, in accordance with an embodiment of the present invention.

DETAILED DESCRIPTION OF EMBODIMENTS

Overview

Figure 1:
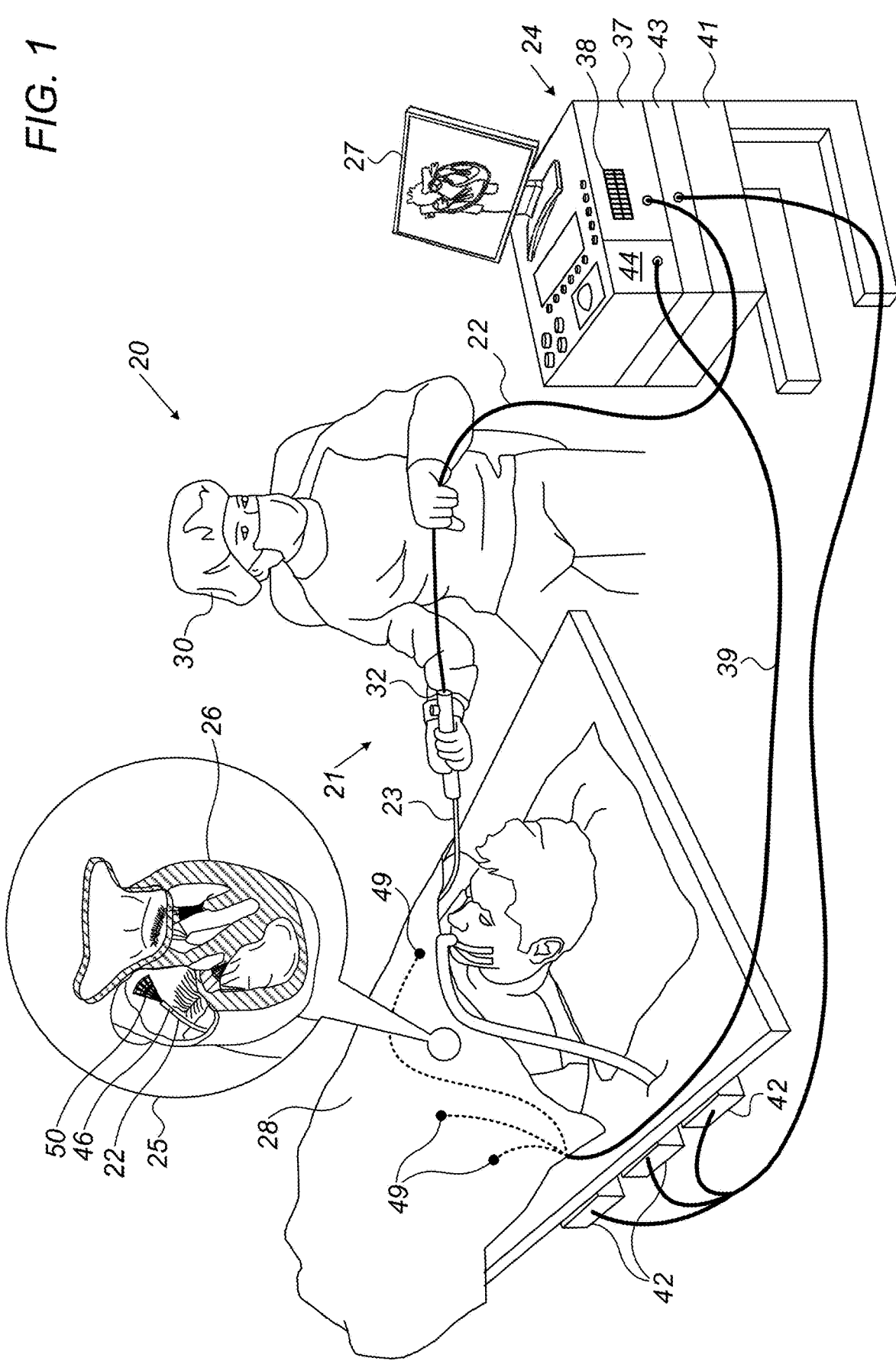
FIG. 1 is a schematic, pictorial illustration of a catheter-based irreversible electroporation (IRE) ablation system comprising a flat array of multiple electrodes, in accordance with an embodiment of the present invention.

Radio-Frequency ablation (using AC signals) or Irreversible electroporation (IRE) also called Pulsed Field Ablation (PFA) that uses DC signals, may be used as an invasive therapeutic modality to kill tissue cells of an organ of a patient by subjecting them to high-voltage pulses. Specifically, RF or PFA have a potential use to kill myocardium tissue cells (e.g., of a cardiac chamber) in order to treat cardiac conditions. Of particular interest is the use of bipolar electric pulses (e.g., using a pair of electrodes of a catheter in contact with tissue) to kill tissue cells between the electrodes. Cellular destruction occurs when the transmembrane potential exceeds a threshold, leading to cell death and thus the development of a tissue lesion.

In order for RF or PFA to be used effectively to ablate selected tissue, it is important to be able to bring the electrodes providing the RF or PFA pulses in contact with selected tissue. While this is possible with substantially any catheter, such as a focal or a basket catheter, if large areas of tissue are to be ablated these catheter types need to be moved between multiple positions to cover the desired area. Moreover, the electrodes must maintain contact with the surface tissue during cardiac wall movement, which, in particular, may increase complexity and the time required to complete the ablation.

Using multiple electrodes that are simultaneously positioned in close proximity one to the other, and in contact with the surface tissue, can increase the effectiveness of the RF or PFA ablation by strengthening an applied electric field, and, optionally, by locally controlling a direction of the electric field to achieve better selectivity.

Embodiments of the present invention that are described hereinafter provide a folding fan catheter that, when unfolded, has a planar fan-like shape that can carry various types of electrodes, such as large-area electrodes to apply RF or PFA pulses to an inner surface of a cavity in an organ of a patient.

In some embodiments, a frame of the folding fan catheter is formed from flat ribbons (e.g., nitinol splines) that can tilt on their pivot point, which allows for easy bending of the planar fan, e.g., at an orthogonal direction to the fan plane. Assuming a preformed folded shape of the frame, the frame may be unfolded by puller wires to separate the splines. Alternatively, the frame may be pre-formed in an unfolded shape and be held folded (e.g., collapsed) in a sheath, assume the fan shape by self-expanding, and rely upon withdrawal back into the sheath to collapse the fan.

A flexible membrane is coupled (e.g., bonded) to the frame, and the electrodes are placed on the membrane. In an embodiment, the membrane comprises a flex printed circuit board (PCB) having the electrodes formed thereon. In its expanded configuration, the splines of the frame maintain the catheter's shape in the fan plane, so that the inter-electrode spacing is fixed and stable. However, the catheter is flexible perpendicularly to the fan plane, so it can conform to an anatomy's variable shape surface.

In some embodiments, where the preformed shape is a folded fan, the puller wires are attached to the extreme ends of the two outer splines in order to pull them apart. The PCB serves as a connective member between the individual splines and thereby determines the fully-deployed geometry of the folding fan catheter as a flat-shape surface. In some embodiments, the splines are rigidly coupled at the distal edge of a shaft of the catheter and can preferentially actuate due to uneven force of a puller wire on each side. Excessive deployment is still limited by the connective materials between splines.

The disclosed fan architecture thus enables the physician to achieve high-quality contact between the electrodes and tissue with a variable geometry. The connective membrane (e.g., flexible PCB) may comprise a set of separate sections, each coupled between two neighboring splines, which, in some designs, may increase the flexibility of the catheter perpendicular to the fan plane.

In some embodiments, the catheter is navigated to a desired area of tissue using an impedance-based tracking system and/or a magnetic-field-based tracking system. Once at the location, the physician utilizes a provided RF or PFA ablation protocol to select which electrodes are to be used for the RF or PFA ablation, as well as IRE pulse parameters.

In an embodiment, a physician inserts the folding fan, collapsed in a sheath, into a cardiac cavity, and then expands the fan to bring it into contact with the inner surface of the cavity. The physician specifies one or more tissue segments to be ablated on the inner surface. In response to the input, a processor selects one or more pairs of the electrodes disposed over the connecting membrane (e.g., the flexible PCB), that, when driven with RF or PFA signals, ablate the specified tissue segments. An RF or PFA pulse generator, controlled by the processor, ablates the specified segments by applying the RF or PFA signals to the electrode pairs.

In an embodiment, the physician receives an indication regarding which electrodes of the catheter's electrode array are in contact with tissue, e.g., using a method that is based on measuring a frequency-response of the electrode (as described in co-assigned U.S. Patent Application Publication 2019/0365463 which is incorporated by reference herein with a copy in the Appendix) and then selects at least these electrodes of the array, as described below.

By using a folding fan catheter, the disclosed invasive cardiac diagnostics and treatment technique can yield an efficient and consistent RF or PFA ablation over a wide area and in complicated tissue anatomy.

System Description

FIG. 1 is a schematic, pictorial illustration of a catheter-based ablation system 20 comprising a folding fan catheter 50, in accordance with an embodiment of the present invention.

System 20 is used to determine the position of folding fan catheter 50, seen in an inset 25 fitted at a distal end of a shaft 22, to RF or PFA ablate target cardiac tissue of a heart 26 of a patient 28.

Physician 30 navigates folding fan catheter 50 to the target tissue location in heart 26 by manipulating shaft 22 using a manipulator 32 near the proximal end of the shaft and/or deflection from a sheath 23. Folding fan catheter 50 is inserted through sheath 23 in a folded (i.e., collapsed) configuration, and only after sheath 23 is retracted does folding fan catheter 50 regain its intended functional shape, for example, by self-expanding into the preformed unfolded shape. By containing folding fan catheter 50 in a folded configuration, sheath 23 also serves to minimize vascular trauma along the way to target location.

Typically, folding fan catheter 50 is used for diagnosis or therapeutic treatment, such as spatially mapping the heart and mapping respective electrical potentials in the heart prior to performing an ablation of heart tissue.

As noted above, folding fan catheter 50 comprises multiple electrodes (seen in FIG. 2) disposed over a large area which have multiple uses (i.e., navigation, sensing, and ablation). The electrodes are connected by wires (not shown) running through shaft 22 to an RF or PFA pulse generator 37 comprising a processor-controlled switching circuitry 38 (e.g., an array of relays) in a console 24. Using circuitry 38, a system processor, or the physician, may select which electrodes to connect to pulse-generator 37 to apply RF or PFA pulses.

Console 24 comprises a processor 41, typically a general-purpose computer, with suitable front end and interface circuits 44 for receiving signals from patch electrodes 49. Signals from electrodes 49 may be electrocardiograms (ECG) and/or position signals used in an Advanced Catheter Location (ACL) position-tracking method described below. Processor 41 is connected to patch electrodes 49, which are attached to the skin of the torso of patient 26, by wires running through a cable 39.

In some embodiments, processor 41 accurately determines position coordinates of the electrodes of folding fan catheter 50 inside heart 26. Processor 41 determines the position coordinates based on, among other inputs, measured impedances between the electrodes (on the catheter) and ACL patch electrodes 49 (i.e., using the ACL method described below). Console 24 drives a display 27 which shows the distal end of catheter position inside the heart.

Processor 41, upon calculating an estimated location of at least a portion of the electrodes of folding fan catheter 50 within the patient's heart, may then associate any given signal received from the electrodes, such as an electrophysiological signal, with the location at which the signal was acquired.

The ACL method of electrode position sensing using system 20 is implemented in various medical applications, for example in the CARTO™ system, produced by Biosense Webster Inc. (Irvine, California) and is described in detail in U.S. Pat. Nos. 7,756,576, 7,869,865, and 7,848,787, whose disclosures are all incorporated herein by reference.

Console 24 further comprises a magnetic-sensing subsystem. Patient 28 is placed in a magnetic field generated by a pad containing magnetic field generator coils 42, which are driven by unit 43. The magnetic fields generated by coils 42 generate position signals in a magnetic sensor 46, seen in inset 25 fitted just proximally to folding fan catheter 50. The signals are further provided as corresponding electrical inputs to processor 41, which uses them to calculate, for example, a roll angle of flat array 50 to correct the ACL-derived electrode positions and/or orientation of the flat array inside the cavity.

The method of position sensing using external magnetic fields is implemented in various medical applications, for example, in the CARTO™ system, produced by Biosense Webster Inc. (Irvine, California) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs dedicated algorithms that enable processor 41 to perform the steps shown in FIG. 3A.

FIG. 1 shows only elements related to the disclosed techniques, for the sake of simplicity and clarity. System 20 typically comprises additional modules and elements that are not directly related to the disclosed techniques, and thus are intentionally omitted from FIG. 1 and from the corresponding description. Another position tracking technique that can be used for tracking the locations of the electrodes on flat array 50 inside heart 26, similar to the ACL described above, is described in U.S. patent application Ser. No. 15/966,514, filed Apr. 30, 2018, now US Patent Application Publication US20190328274 titled "Improved Active Voltage Location (AVL) Resolution," which is assigned to the assignee of the present patent application, which document is incorporated by reference with a copy provided in the Appendix.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. The term "distal" and "proximal" are relative term in relation to the operator of the device such that "distal" indicates the region or portion of the device further away from the operator and "proximal" indicates that the region or portion of the device is closer to an operator than a distal region.

Folding Fan Catheter with Electrode Array

Figures 2A, 2B:
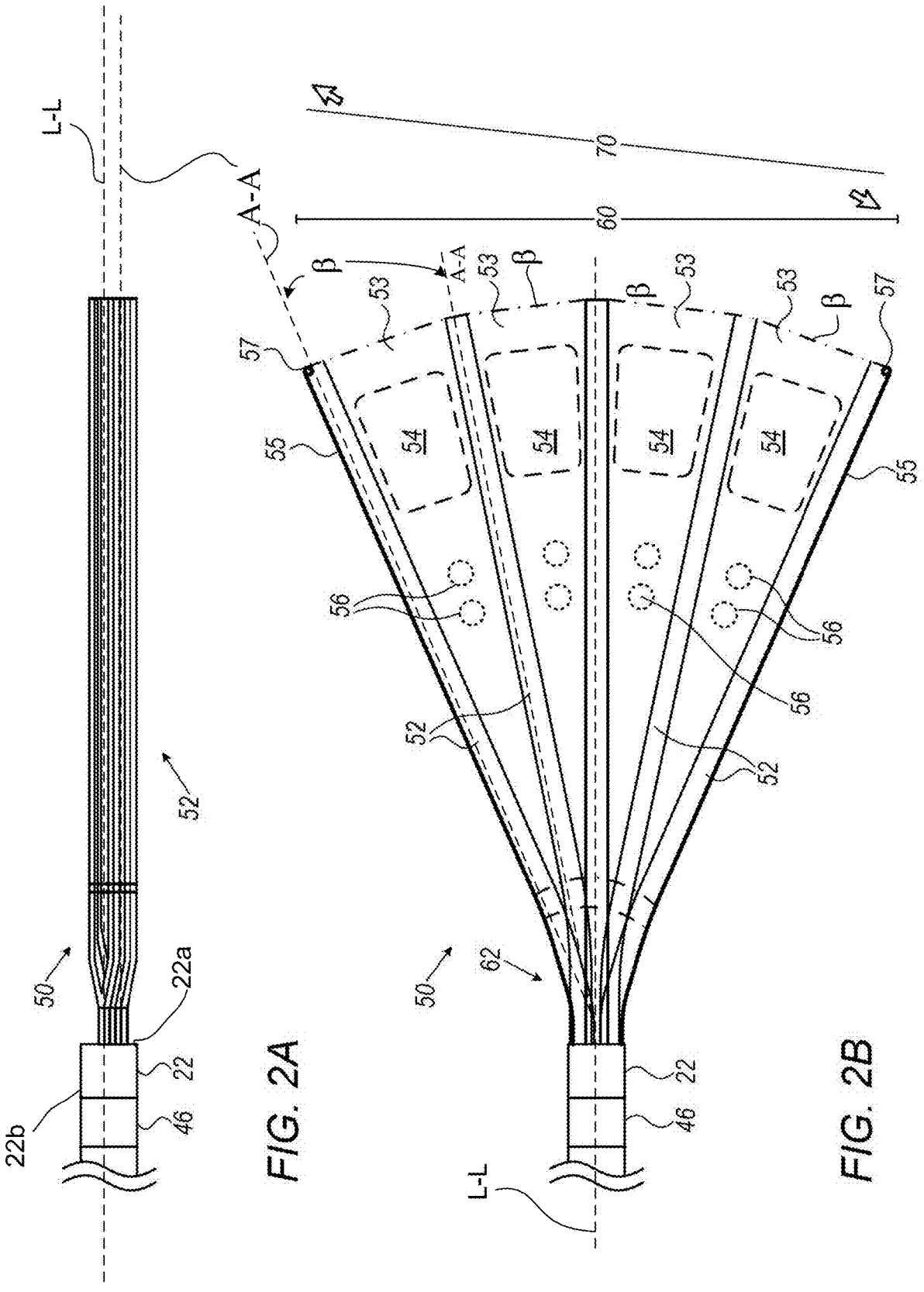
FIGS. 2A and 2B are side views of the folding fan catheter of FIG. 1, in folded and unfolded layouts, respectively, in accordance with an embodiment of the present invention.

FIGS. 2A and 2B are side views of folding fan catheter 50 of FIG. 1, in folded and unfolded layouts, respectively, in accordance with an embodiment of the present invention.

Figure 3A:
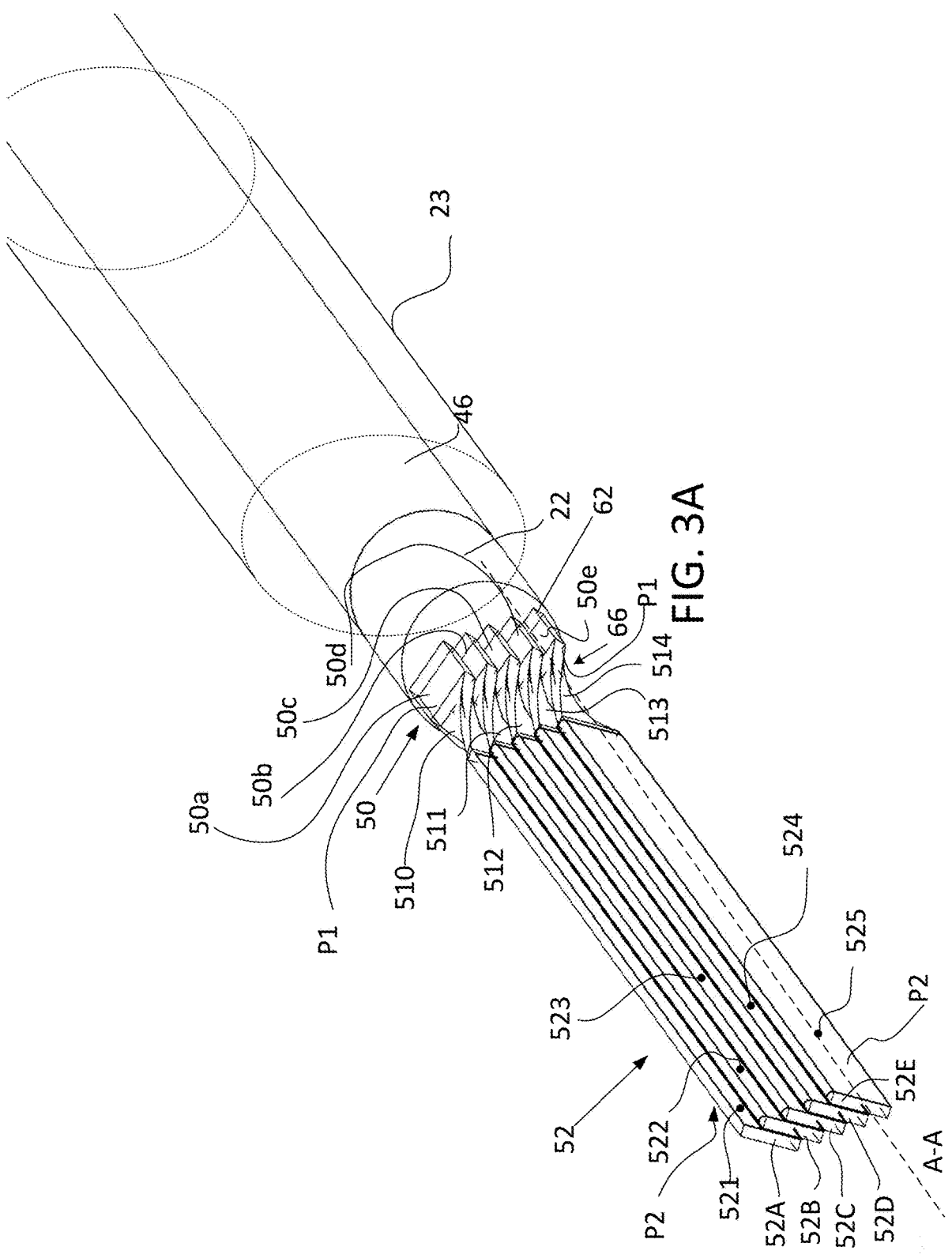
FIG. 3A is an isometric view of the folding fan catheter in the folded layout of FIG. 2B, in accordance with an embodiment of the present invention.

In the shown embodiment, resilient frame member 52 of the catheter are collapsed in FIG. 2A and expanded in FIG. 2B, in a form of a planar surface. To this end, the resilient frame member 52 are bent by about 90° at their base, as shown in FIG. 3E. In the second or unconstrained configuration of FIG. 2B, it is noted that each frame member 52 is separated to its adjacent neighbor frame member by an angle ß of about 5 degrees to about 15 degrees as measured at the intersection of the frame members proximate shaft 22. One preferred embodiment utilizes about 10 degrees. In this configuration, the frame members extend along its axis A-A at respective angles to the longitudinal axis L-L to define a substantially planar triangular array of five-finger like frame members 52 with a membrane 53 disposed between the finger-like frame members 52. At least one of electrodes 54 and 56 can disposed on the membrane 53. Electrode 54 or 56 can be formed from a flexible circuit electrode. Electrical trace can be used to connect the electrode(s) back to the proximal handle or the electrical trace can be connected to the frame member which can act as a conductor in the case of the frame member being made from a biocompatible metal. Alternatively, wirings can be utilized instead of PCB traces.

As further seen, catheter 50 comprises puller wires 55, each of which attached to an extreme end 57 of an outer spline, in order to pull the two outer spines apart, if the self-configurable preformed shape is a folded fan.

Figure 3B:
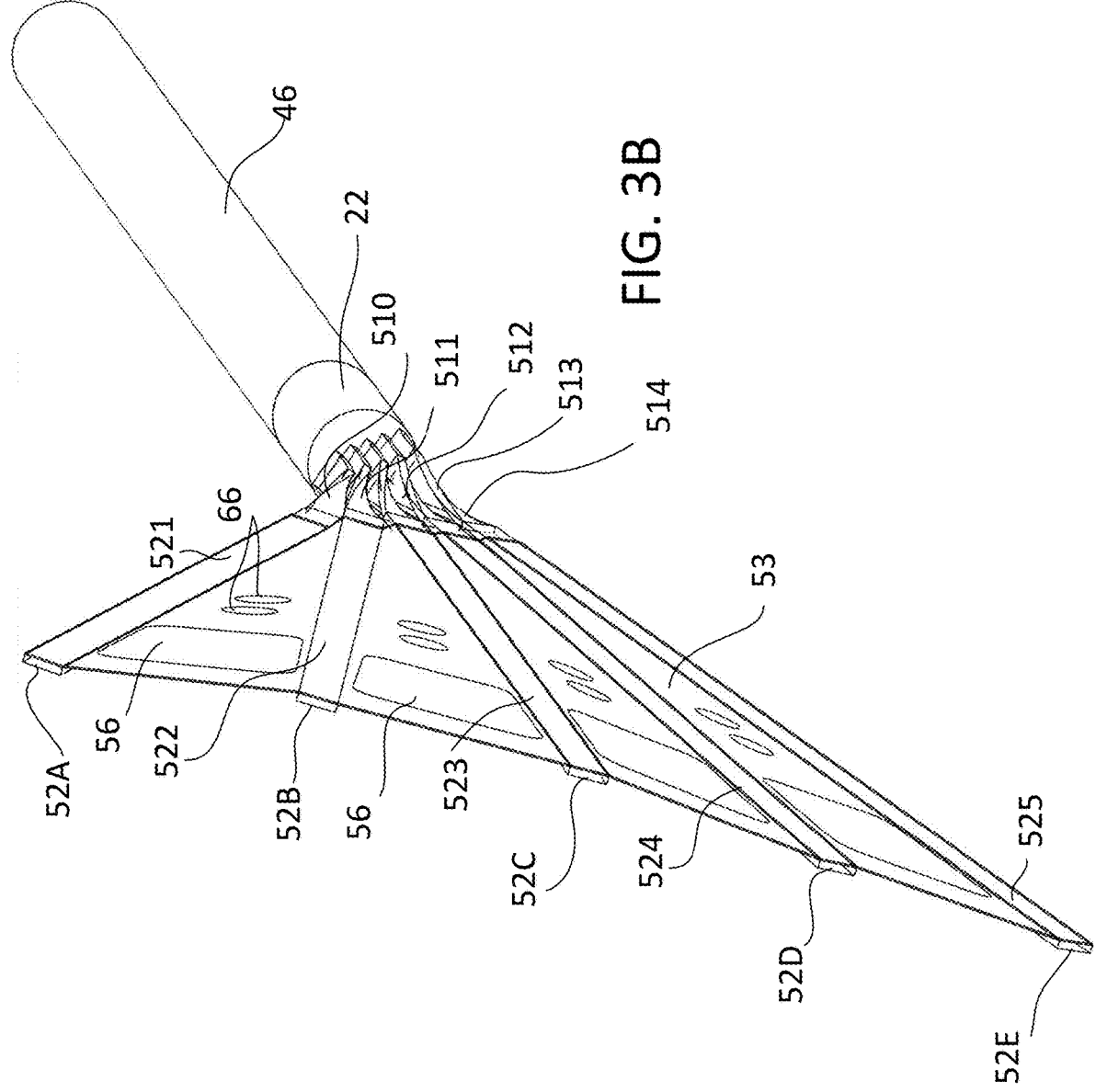
FIG. 3B is an isometric view of the catheter in an unfolded configuration.
Figures 3C, 3D, 3E, 3F:
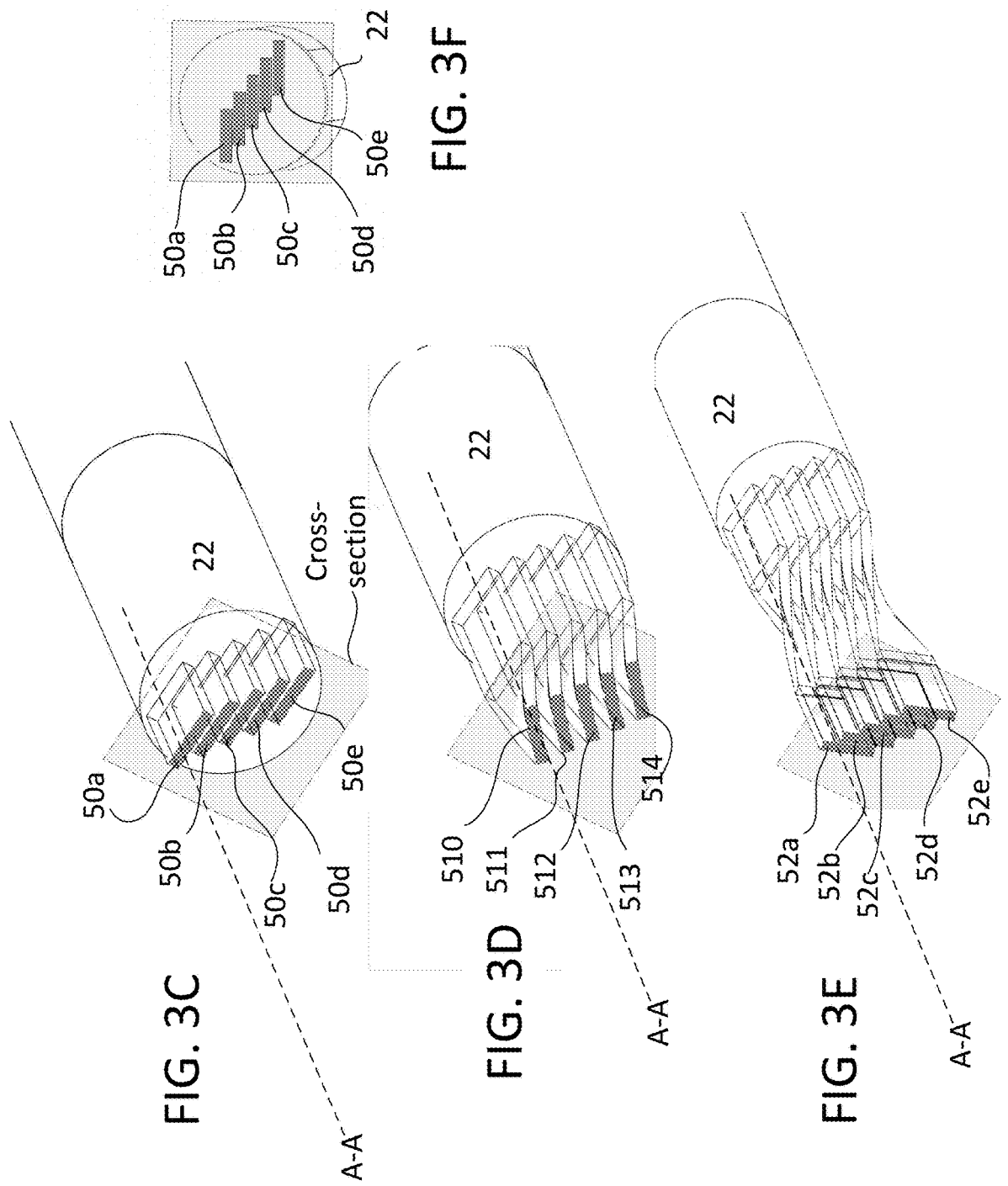
FIG. 3C is a perspective view of an orthogonal cross-section to show the stacked parallel stair-like arrangement of the frame members.
FIG. 3D is another cross-sectional view distally of the frame members in FIG. 3C to show the cross-section of the twist to each frame members.
FIG. 3E is another cross-sectional view distally of the frame members in FIG. 3D.
FIG. 3F is a cross-sectional plan view from an observer on the longitudinal axis of the catheter to show details of the stair-step parallel frame members.

A flexible PCB 53 is coupled to spines 52 and serves as a connective member between the individual splines and thereby determines a full deployment (60) of the folding fan catheter, shown here in FIG. 3B. In other embodiments, excessive deployment is limited by connective materials other than PCB 53 (e.g., by a membrane) between selected splines.

Furthermore, in the embodiments, the splines are rigidly attached at shaft 22 end location 62 that can preferentially bend due to the force of a puller wire on each side. Thus, the fan architecture enables a deployable plane which can be actuated (70) out of the fan plane by the physician to achieve a best contact in tissue with a variable geometry.

As seen in FIG. 3B, flexible PCB 53 is disposed with large area electrodes 54, the primary use of which is ablation, such as Radio-Frequency ablation or irreversible electroporation with PFA. Additional, smaller electrodes 56 are primary used for EP sensing (i.e., to record electrical signals from cardiac tissues). However, any electrode may be used for either diagnosis or treatment, depending, for example, on user selection.

In its expanded configuration of FIG. 3B, the flat frame spines (e.g., ribbons) maintain the catheter shape in the fan plane, so that the inter-electrode spacing is fixed and stable. However, the catheter is flexible perpendicular to the fan plane.

FIGS. 2A and 2B shows only elements related to the disclosed techniques, for the sake of simplicity and clarity. Folding fan catheter 50 may, for example, also be disposed with temperature sensors and/or contact force sensors.

Processor 41 may be used to select any electrode pair of electrodes 54 and 56, and subsequently command switching assembly 38 to connect the electrodes to RF or PFA pulse-generator 37 to apply bipolar RF or PFA pulses between, for example, pairs of electrodes 54 and separately apply bipolar RF or PFA pulses between pairs of electrodes 56. As another example, the processor may select an electrode pair 54-56 of a same member to switch to an orthogonal direction of electric field.

As applied to IRE ablation, processor 41 is used to select an IRE ablation protocol comprising the bipolar IRE pulses. An example of IRE ablation settings that may be used with electrode 54 and 56 is given by Table I:

TABLE I

| Parameter | Range |
| --- | --- |
| Preset IRE peak voltage | 500-3000 V |
| Pulse width | 0.5-10 microsecond |
| Repetition rate | 1-400 Hz |
| Number of pulses | 10-2000 |
| Directon of electrical field | User selected |

As seen in the protocol of Table I, the direction of applied electric fields is user selected.

FIG. 3A is an isometric view of the folding fan catheter in the unfolded layout of FIG. 2B, in accordance with an embodiment of the present invention.

As seen in FIG. 3A, each of the strip-shaped frame members 521, 522, 523, 524, 525 is configured to bend or twist (66) about a longitudinal axis A-A of the spline when the frames 521-525 are in a constrained or folded configuration. Due to the twist of the frame members 521-525, a bias force is generated when the frame members 521-525 are collapsed or constrained in sheath 23. When the frames 521-525 unfolds or is unconstrained by a sheath 23, such that when the frame is unfolded, the strip-shaped splines lie in a plane of the fan-shaped surface, shown here in FIG. 3B. Therefore, the frame that is formed from flat nitinol ribbons 52 which have the 90° rotation (66) at their pivot point, can easily be controlled by puller wires (seen in FIG. 2) so that the frame, if pre-formed collapsed, is expanded into the required flat surface. In FIG. 3A, each of the plurality of frame members 521, 522, 523, 524, 525 has, in the first configuration, a planar surface "P1" (the underside surface of 50e) that extends from a proximal portion 50e affixed to the distal end 22a of the shaft 22 to a terminal end portion (indicated as "P2"), the planar surface at the terminal end portion being disposed approximately 90 degrees with respect to the planar surface at the proximal portion. It is noted that surface P1 can be either the top surface or the bottom surface of each frame member 52. For example, frame member 50a has top surface P1 visible which top surface is twisted along the length of frame member 521 to arrive at planar surface P2 that is about 90 degrees with respect to P1. That is, each of the frame member 521, 522, 523, 524, 525 have three distinct portions. Taking frame member 521 as one example, it is noted that frame member 521 has (a) a first fixed proximal planar portion 50a, (b) a second twisted intermediate portion 510, and (c) a final planar portion 52a. These portions contribute to the ability of the distal assembly to unfold into an unfolded generally planar triangular configuration.

The unfolded layout shown in FIG. 3A is brought purely by way of example. For example, other means to form the disclosed unfolded fan catheter may be used, such as using one or more axes of rotation to couple frame members 521-525 to the shaft 22 distal end.

Certain characteristics of the frame members are of note when the frame members 512-525 are orthogonally cross-sectioned along a length of the frame members in FIGS. 3C, 3D and 3E. In FIG. 3C, it can be seen that the fixed proximal fixed portions 50a, 50b, 50c, 50d, 50e are planar members that are parallel to each other in a stacked stair-like configuration shown in FIG. 3F (FIG. 3F being an end view of the frame members from an observer looking along the longitudinal axis A-A of FIG. 3C in which shaft 22 is visible). In FIG. 3D of a distally located orthogonal cross-section, one can see that the cross-sections 510, 511, 512, 513, 514 are bent or twisted with respect to the counterpart cross-sections 50a, 50b, 50c, 50d, 50e in FIG. 3C. Each of frame members 521-525 is twisted until the cross-section of frame member takes on the final configuration shown in orthogonal sectioned view of FIG. 3E. The frame members 521-525 at this point on will have the cross-sections referenced as 52a, 52b, 52c, 52d, 52e. Of note is that the final distal cross-sections 52a-52e are substantially perpendicular to the proximal cross-sections 50a-50e. While the cross-section of each frame member is shown as generally rectangular, it is well within the scope of the invention that the cross-section can be of any suitable cross-section (e.g., square, circular, polygonal) as long as (a) the cross-sections can be a parallel stacked stair-like configuration (FIG. 3E) and (b) the frame members do not bind or interfere with each other in the unconstrained or uncompressed open configuration. The frame members are made of a suitable biocompatible material, such as for example, biocompatible metals or shape memory material such as nitinol.

FIG. 4 is a flow chart that schematically illustrates a method of irreversible electroporation (IRE) using folding fan catheter 50 of FIG. 2B, in accordance with an embodiment of the present invention. The algorithm, according to the presented embodiment, carries out a process that begins when physician 30 navigates flat array 50 to a target tissue location in an organ of a patient, such as an atrial septum, using, for example, sensor 46, at a flat array navigation step 102.

Next, physician 30 unfolds flat array 50, at a catheter 50 unfolding step 104. Subsequently, physician 30 brings the fan with its electrodes into contact with tissue, at a tissue contacting step 106.

At an electrode physical contact determination and selection step 108, processor 41 determines which of electrodes 54/56 are in contact with tissue, and physician 30 selects at least a portion of these electrodes to apply IRE pulses.

Next, at an electrode configuration setup step 110, processor 41 receives user inputs, such as of step 108 and/or in the form of one or more prespecified directions (e.g., relative to a longitudinal axis of the distal end) along which the electric field should be applied to tissue. Based on the required electric field directions, processor 41 determines between which pairs of the selected electrodes 54/56 to apply, for example, RF or IRE pulses.

Next, processor 41 controls switching assembly 38 to connect the pairs of electrodes to IRE pulse-generator 37 according to the determined configuration, at pair electrodes connecting step 112.

Processor 41 then receives (e.g., uploads from memory) an ablation protocol comprising the RF or IRE ablation parameters (e.g., number and peak voltage of pulses), at an RF or IRE parameter selection step 114. At this stage the physician may modify some of the parameters. Alternatively, the protocol may have been loaded earlier in the procedure and is ready at this stage.

Finally, processor 41 commands RF or IRE pulse generator 37 to apply the directional RF or IRE pulses to tissue via the selected pairs of electrodes 55, at an RF or IRE treatment step 116.

FIG. 4 is an example flow that is depicted purely for the sake of clarity. Additional steps may be included, such as, in the absence of sufficient information regarding myocardial cell orientations, processor 41 controlling switching assembly 38 to apply RF or PFA pulses at multiple (typically two) different orientations to the same region of tissue. For example, processor 41 may control switching assembly 38 to apply the RF or PFA pulses at two orthogonal directions.

Although the embodiments described herein mainly address cardiac applications, the methods and systems described herein can also be used in other medical applications, such as in neurology and otolaryngology.

It will be thus appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. A catheter comprising:
    a shaft extending along a longitudinal axis from a proximal portion to a distal end;
    a plurality of frame members attached to the distal end, the plurality of frame members having a first configuration in which the frame members are parallel to one another and a second configuration in which the frame members extend at respective angles to the longitudinal axis such that the plurality of frame members together define a platform that is a substantially planar triangular array;
    a plurality of membranes, a respective membrane of the plurality of membranes disposed between any two adjacent frame members of the plurality of frame members; and
    a plurality of electrodes, each electrode disposed over a respective membrane of the plurality of membranes.

2. The catheter of claim 1, in which each of the plurality of frame members in the first configuration includes a planar surface that extends from a proximal portion affixed to the distal end of the shaft to a terminal end portion, the planar surface at the terminal end portion being disposed approximately 90 degrees with respect to the planar surface at the proximal portion.

3. The catheter of claim 1, wherein the plurality of frame members comprises a plurality of splines.

4. The catheter of claim 3, wherein the plurality of frame members is configured to collapse upon withdrawal back into the shaft.

5. The catheter of claim 1, wherein each frame member of the plurality of frame members extends along a respective longitudinal axis and comprises a proximal planar portion, a distal planar portion, and a twisted portion disposed therebetween, the twisted portion being twisted about the respective longitudinal axis.

6. The catheter of claim 1, further comprising:
    puller wires attached to a distal end of at least one frame member of the plurality of frame members, the puller wires configured to, when pulled in a proximal direction, pull the plurality of frame members apart to cause the plurality of frame members to transition to the second configuration.

7. A method of manufacturing a folding fan catheter, the method comprising:

fixing, to a distal end of a shaft, a resilient foldable frame configured to be unfolded so as to assume a fan shape, the resilient foldable frame comprising a plurality of frame members having a first configuration in which the frame members are parallel to one another and a second configuration in which the frame members extend at respective angles to a longitudinal axis of the shaft such that the plurality of frame members together define a platform that is a substantially planar triangular array defining the fan shape;

coupling one or more flexible surfaces to the frame, to form a fan-shaped surface when the frame is unfolded; and disposing a plurality of electrodes over the one or more flexible surfaces, wherein the electrodes are configured to contact tissue.

8. The method of manufacturing according to claim 7, wherein the resilient foldable frame is made at least partially of a shape memory alloy having a self-configurable pre-formed shape comprising, when unconstrained, one of a folded fan shape and an unfolded fan shape.

9. The method of manufacturing according to claim 8, wherein the preformed shape of the frame comprises the folded fan shape, the method further comprising attaching puller wires to distal ends of the frame, wherein the wires are configured to, when pulled, pull the frame apart into the unfolded fan shape.

10. The method of manufacturing according to claim 8, wherein:

the plurality of frame members comprises a plurality of splines, the splines are strip-shaped, and are configured to overlap when the frame is folded, and each strip-shaped spline is configured to bend about a longitudinal axis of the spline when the frame unfolds, such that when the frame is unfolded, the strip-shaped splines lie in a plane of the fan-shaped surface.

11. The method of manufacturing according to claim 10, wherein each spline of the plurality of splines extends along a respective longitudinal axis and comprises a proximal planar portion, a distal planar portion, and a twisted portion disposed therebetween, the twisted portion being twisted about the respective longitudinal axis.

12. The method of manufacturing according to claim 8, wherein the preformed shape of the frame comprises the unfolded fan shape, and wherein the frame is configured to be collapsed upon withdrawal back into a sheath.

13. The method of manufacturing according to claim 7, wherein the one or more flexible surfaces comprise one or more flexible printed circuit boards (PCBs), and wherein disposing the electrodes comprises forming the electrodes in one or more electrically-conductive layers of the PCBs.

14. A method, comprising:

inserting into a cavity of an organ of a patient, through a sheath, a folding fan catheter fixed to a distal end of a shaft, the folding fan catheter comprising:

a resilient foldable frame, which is fixed to the distal end of the shaft and is configured to be unfolded so as to assume a fan shape, the resilient foldable frame comprising a plurality of frame members having a first configuration in which the frame members are parallel to one another and a second configuration in which the frame members extend at respective angles to a longitudinal axis of the shaft such that the plurality of frame members together define a platform that is a substantially planar triangular array defining the fan shape;

one or more flexible surfaces, coupled to the frame to form a fan-shaped surface when the frame is unfolded; and a plurality of electrodes that are disposed over the one or more flexible surfaces and are configured to contact tissue;

after the folding fan catheter exits the sheath in the cavity and the resilient foldable frame assumes the fan shape, making contact between the plurality of electrodes and tissue, and performing a medical procedure using the electrodes.

15. The method according to claim 14, wherein the resilient foldable frame is made at least partially of a shape memory alloy having a self-configurable preformed shape comprising, when unconstrained, one of a folded fan shape and an unfolded fan shape.

16. The method according to claim 15, wherein inserting the catheter comprises, if the preformed shape comprises the folded fan shape, pulling the frame apart by pulling puller wires attached to extreme ends of splines of the frame.

17. The method according to claim 15, wherein inserting the catheter comprises, if the preformed shape comprises the unfolded fan shape, allowing the frame to self-expand.

18. The method according to claim 14, wherein the plurality of frame members comprises a plurality of splines that are strip-shaped.

19. The method according to claim 18, wherein each spline of the plurality of splines extends along a respective longitudinal axis and comprises a proximal planar portion, a distal planar portion, and a twisted portion disposed therebetween, the twisted portion being twisted about the respective longitudinal axis.

20. The method according to claim 14, wherein the one or more flexible surfaces comprise one or more flexible printed circuit boards (PCBs).

* * * * *